US012571812B2

(12) United States Patent (10) Patent No.: US 12,571,812 B2

Ghouze et al. (45) **Date of Patent: \*Mar. 10, 2026**

(54) PARALLEL CELL PROCESSING METHOD AND FACILITY

(71) Applicant: Global Life Sciences Solutions USA LLC, Marlborough, MA (US)

(72) Inventors: Firman Ghouze, Singapore (SG); Philip Vanek, Ashburn, VA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 60 days.

This patent is subject to a terminal disclaimer.

(21) Appl. No.: 18/531,157

(22) Filed: Dec. 6, 2023

(65) Prior Publication Data

US 2024/0118299 A1 Apr. 11, 2024

Related U.S. Application Data

(63) Continuation of application No. 17/101,041, filed on Nov. 23, 2020, now Pat. No. 11,879,903, which is a (Continued)

(30) Foreign Application Priority Data

Aug. 29, 2014 (GB) ...................................... 1415329

(51) Int. Cl.
$G01N\ 35/00$ (2006.01)
$A61K\ 35/12$ (2015.01)

(52) U.S. Cl.
CPC ......... *$G01N\ 35/0099$* (2013.01); *$A61K\ 35/12$* (2013.01); *$G01N\ 35/00732$* (2013.01); (Continued)

(58) Field of Classification Search
CPC .................................................. G01N 35/0099
See application file for complete search history.

(56) References Cited

U.S. PATENT DOCUMENTS 4,514,415 A 4/1985 Wenk et al.
5,876,670 A 3/1999 Mitsumaki et al.
(Continued)

FOREIGN PATENT DOCUMENTS

EP 0915341 A2 5/1999
EP 1238671 A1 9/2002
(Continued)

OTHER PUBLICATIONS

International Search Report and Written Opinion regarding International Application No. PCT/EP2015/066666, mail date Jan. 19, 2016, 15 pages.
(Continued)

*Primary Examiner* — Rosanne Kosson
(74) *Attorney, Agent, or Firm* — Eversheds-Sutherland (US) LLP

(57) ABSTRACT

The present invention provides improved methods, facilities and systems for parallel processing of biological cellular samples in an efficient and scalable manner. The invention enables parallel processing of biological cellular samples, such as patient samples, in a space and time efficient fashion. The methods, facilities and systems of the invention find particular utility in processing patient samples for use in cell therapy.

7 Claims, 4 Drawing Sheets

Related U.S. Application Data continuation of application No. 16/245,924, filed on Jan. 11, 2019, now Pat. No. 10,877,055, which is a continuation of application No. 15/327,800, filed as application No. PCT/EP2015/066666 on Jul. 21, 2015, now Pat. No. 10,184,949.

(60) Provisional application No. 62/026,748, filed on Jul. 21, 2014.

(52) U.S. Cl.
CPC .................. *B01J 2219/00587* (2013.01); *B01J 2219/00743* (2013.01); *G01N 2035/00326* (2013.01); *G01N 2035/00752* (2013.01); *G01N 2035/00762* (2013.01); *G01N 2035/00782* (2013.01); *G01N 2035/00811* (2013.01); *G01N 2035/00831* (2013.01)

(56) References Cited

U.S. PATENT DOCUMENTS

| | | | |
|---|---|---|---|
| 5,928,952 | A | 7/1999 | Hutchins et al. |
| 5,972,295 | A | 10/1999 | Hanawa et al. |
| 6,861,954 | B2 | 3/2005 | Levin |
| 8,005,622 | B2 | 8/2011 | Hauck et al. |
| 8,032,306 | B2 | 10/2011 | Hauck et al. |
| 8,099,297 | B2 | 1/2012 | Brevnova et al. |
| 8,204,694 | B2 | 6/2012 | Hauck et al. |
| 8,229,675 | B2 | 7/2012 | Csore et al. |
| 8,484,049 | B2 | 7/2013 | Mullenger et al. |
| 8,656,670 | B2 | 2/2014 | Mouzannar |
| 8,666,762 | B2 | 3/2014 | Kasprisin et al. |
| 2003/0175242 | A1 | 9/2003 | Gruenberg |

| | | | |
|---|---|---|---|
| 2005/0184153 | A1 | 8/2005 | Auchinleck |
| 2008/0189045 | A1 | 8/2008 | Moore |
| 2008/0253927 | A1 | 10/2008 | Burow et al. |
| 2008/0254545 | A1 | 10/2008 | Kitaoka |
| 2009/0117620 | A1 | 5/2009 | Fritchie et al. |
| 2009/0299763 | A1 | 12/2009 | Sakurada |
| 2010/0049542 | A1 | 2/2010 | Grant et al. |
| 2010/0099133 | A1 | 4/2010 | Egle et al. |
| 2012/0149059 | A1 | 6/2012 | Shah |
| 2012/0270336 | A1 | 10/2012 | Haga |
| 2013/0018356 | A1 | 1/2013 | Prince et al. |
| 2013/0079236 | A1 | 3/2013 | Holmes |

FOREIGN PATENT DOCUMENTS

| | | |
|---|---|---|
| EP | 1850289 A1 | 10/2007 |
| EP | 2263183 A1 | 12/2010 |
| EP | 2610621 A | 7/2013 |
| JP | 2003-180662 A | 7/2003 |
| JP | 2011-045259 A | 3/2011 |
| JP | 2011-115107 A | 6/2011 |
| WO | 1998028700 A1 | 7/1998 |
| WO | 2006129312 A2 | 12/2006 |
| WO | 2007105846 A1 | 9/2007 |
| WO | 2008018671 A1 | 2/2008 |
| WO | 2008/152204 A1 | 12/2008 |
| WO | 2014093838 A2 | 6/2014 |
| WO | 2014/110587 A1 | 7/2014 |

OTHER PUBLICATIONS

GB Search Report regarding GB Application No. 1415329.0, dated May 21, 2015, 5 pages.

Japanese Pre-Appeal Report for JP Application No. 2019-017792 mailed Mar. 30, 2020 (8 pages, with English translation).

Japanese Office Action for JP Application No. 2021-102353, mailed Jun. 20, 2022 (12 pages, with English translation).

FIGURE 1

Custody chain; maintains integrity of physical and identity separation

FIGURE 2

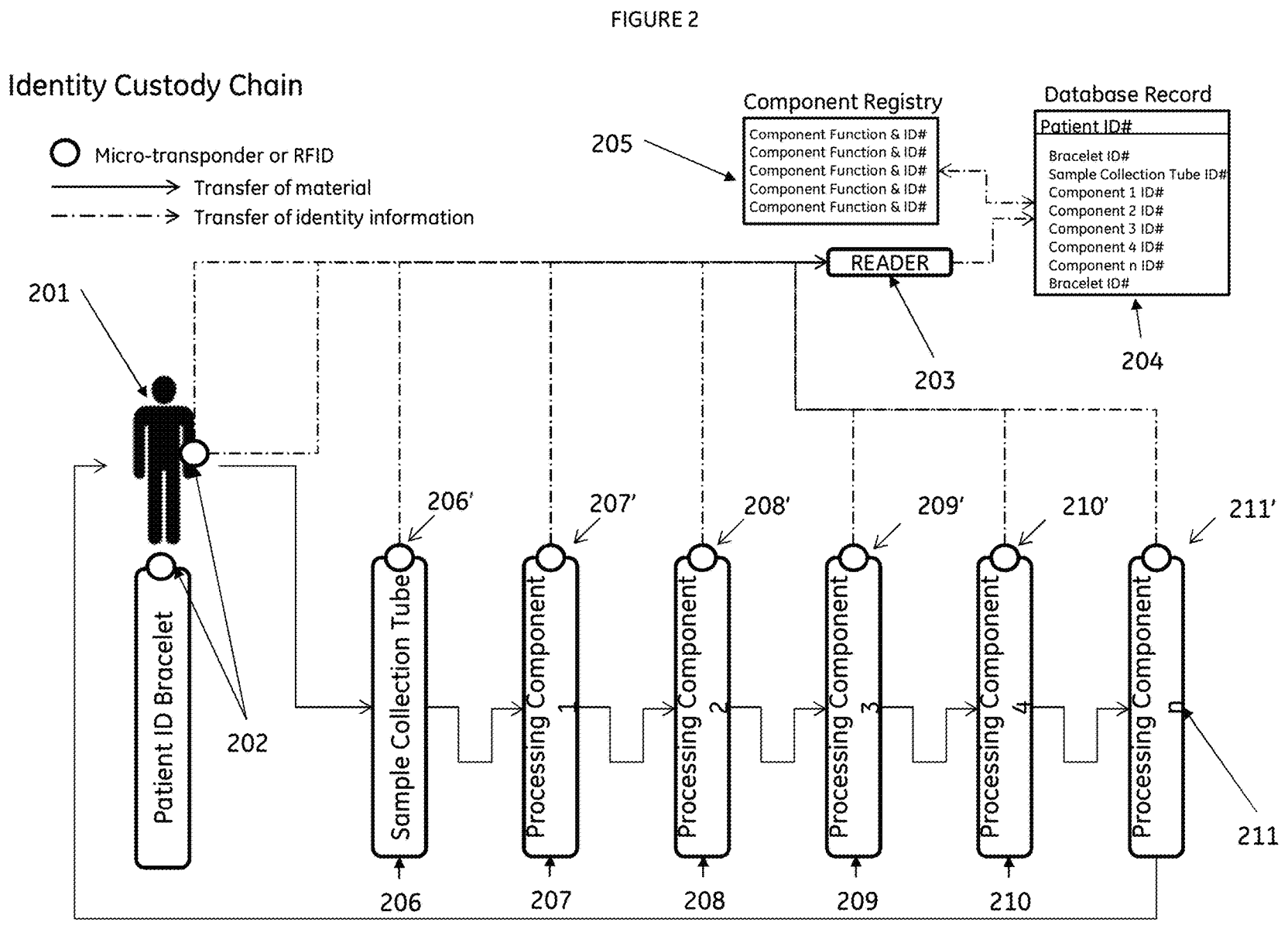

Identity Custody Chain

◯ Micro-transponder or RFID
→ Transfer of material
-·-·-→ Transfer of identity information

Database Record

| Patient ID# |
| --- |
| Bracelet ID# |
| Sample Collection Tube ID# |
| Component 1 ID# |
| Component 2 ID# |
| Component 3 ID# |
| Component 4 ID# |
| Component n ID# |
| Bracelet ID# |

204

Component Registry

| |
| --- |
| Component Function & ID# |
| Component Function & ID# |
| Component Function & ID# |
| Component Function & ID# |
| Component Function & ID# |

205

READER

203

Processing Component n — 211', 211

Processing Component 4 — 210', 210

Processing Component 3 — 209', 209

Processing Component 2 — 208', 208

Processing Component 1 — 207', 207

Sample Collection Tube — 206', 206

Patient ID Bracelet — 202

PARALLEL CELL PROCESSING METHOD AND FACILITY

CROSS-REFERENCE TO RELATED APPLICATIONS

This patent application is a continuation of U.S. application Ser. No. 17/101,041, filed Nov. 23, 2020, which is a continuation of U.S. application Ser. No. 16/245,924, filed Jan. 11, 2019, allowed, which is a continuation of U.S. application Ser. No. 15/327,800, filed Jan. 20, 2017, now U.S. Pat. No. 10,184,949, issued Jan. 22, 2019, which claims priority to PCT Application No. PCT/EP2015/066666, filed Jul. 21, 2015, which claims priority benefit of U.S. Provisional Application No. 62/026,748, filed Jul. 21, 2014 and Great Britain Application No. 1415329.0, filed Aug. 29, 2014, each of which is incorporated herein by reference in their entireties.

BACKGROUND TO THE INVENTION

Cell therapy is a key area of medical advance in the treatment of a range of conditions and diseases including cancer. Autologous cell therapy, the treatment of a patient with the patient's own cells, is an increasingly used and improving method for combatting cancers, including melanoma and leukaemia, which are refractory to conventional drug treatment. One area of autologous cell therapy, immunotherapy, uses selection and expansion of cells from the patient's own immune system to target and attack cancer cells, effectively boosting many fold the patient's immune response to destroy the cancer cells.

To achieve immunotherapy and other forms of cell therapy samples of cells taken from a patient, typically in the form of a blood sample, must be processed through a complex workflow to isolate, engineer, concentrate and/or expand by culture the cells which will form the therapeutic material administered back into the patient. Carrying out the cell processing workflow requires a series of operations performed using a variety of processing methods, machines and instruments, each with a unique role in the overall process. The process may comprise steps of different duration and complexity requiring varying degrees of operator intervention and skill and all operations must be carried out under sterile conditions to prevent microbial, viral or other contamination of the patient sample. The process must also be carried out using means which maintain the integrity of the patient's material and prevent partial or whole cross-contamination or mixing of patient samples to prevent a patient receiving a therapeutic preparation which is not wholly derived from the patient's own cells.

To achieve the sterility and integrity of patient material all processing operations are typically performed in a laboratory or clean room furnished with equipment, for example laminar air flow cabinets, which allow the material to be manipulated using open containers in a sterile environment to minimise the risk of biological or other contamination from the environment. To prevent mixing of patient materials and maintain the integrity of the sample identity the processing operations are carried out in separate and isolated processing rooms or units each of which duplicates the equipment and processes of the others. Each duplicated unit provides the necessary sterile working environment and is furnished with all of the sample handling and processing equipment required to process one single patient sample at one time. As each unit is used only for one patient sample at a time, a facility processing many patient samples requires a number of identical processing units and therefore duplicates costs of providing space, services and equipment, such costs scaling linearly with the number of patient samples to be processed. These costs are seen as a major barrier to the further development of cell therapy and the expansion of use of cell therapy in a larger patient population as the duplicative approach does not provide economies of scale to reduce treatment costs.

In addition to the high setting up and running costs and the high costs of capacity expansion, the duplication of processing units is extremely inefficient in use of space and equipment. Since each stage of the processing workflow takes a different period of time, the overall throughput of the workflow is determined by the rate limiting step, i.e. the longest step in the process, and therefore most of the resources available in each duplicated processing unit are underutilised for much of the time taken to process a sample through the workflow. In a typical immunotherapy processing workflow the process of cell expansion, the culture and growth of cells from the thousands of cells isolated from a patient's blood sample to the millions or billions of cells required for a therapeutic dose, may take up to two weeks. In contrast, the cell isolation and concentration steps used at the beginning and end of the workflow may take only a few minutes or hours. Consequently in the standard cell processing facility, using duplication of processing units, a large amount of space and capital equipment used for short term operations, such as cell isolation, stands idle during the cell expansion operation.

In addition to the cost and efficiency shortcomings of the standard duplicated unit approach described above, processing samples in a laboratory or clean room using open containers still retains a risk of bacterial, viral or other contamination of the sample, does not preclude loss of part or all or the patient sample or processed material at any stage in the process due to operator error, and retains the opportunity for cross-contamination of samples by residual material remaining in the processing unit from a previous patient sample or processed material.

What is required is a means to process patient material in a fashion which maximises the efficiency of the processing workflow for time and cost allowing the process to be operated for multiple patients with economies of scale that enable use of cell therapy in a larger patient population. Such means must retain the fundamental key principles of preventing contamination, mixing, loss of identity or other events which interfere with the physical and identity integrity of the patient sample and processed therapeutic material.

These features and benefits are not provided by current cell therapy processing facilities and such features and benefits are not described or suggested by the prior art.

US20030175242 describes systems and methods for manufacturing and distributing cell therapy products. The methods include establishing a central processing facility and a plurality of satellite facilities administered under a single license for conducting cell therapy, collecting source material at one of the satellite facilities from a first subject, transporting the source material from the first subject and delivering the source material to the central processing facility, processing the material at the central processing facility to produce a therapy product for administration to the same first subject, transporting the therapy product back to the satellite facility and administering the therapy product to the same first subject.

U.S. Pat. No. 8,656,670 provides a system, workflow and facilities for tissue banks comprising a central access corridor having spaces on both sides for public and private diagnostic areas, public and private clean room areas for processing, culturing and other manufacturing steps and public and private storage areas, wherein all public facilities are on one side of the central access way and private facilities are on the other side provided with air locked sample pass through connections between each area.

WO1998028700 describes a method for quality management in a cell therapy process of sampling cells from a patient, specific treatment of these cells according to a specific treatment protocol, and reinfusion of cells into the patient. The method comprises steps of identifying entities involved in the therapeutic process; steps of sequential and conditional validation of the therapeutic process; and steps of quality control. The steps of identification, validation and control are carried out for each batch of samples taken from a given patient.

WO2006129312 describes a method for automated cell processing, including receiving a tissue sample containing a multiplicity of cells belonging to multiple cell types, and automatically increasing both the proportion of cells of cell type.

WO2007105846 describes a method for using a cell therapy facility and a franchise market business method wherein the facility comprises a plurality of separately prefabricated units having individual-specific functions and having an entrance and exit separately partitioned from each other so as to minimize occurrence of contamination.

WO2008018671 describes a facility for cell manipulation and cultivation for production of cell therapy products comprising a room with a L-shaped partition and a clean bench device placed inside the partition, including three clean benches to prevent contamination of cells.

EP1850289 describes the use of RFID (Radio Frequency Identification) in the workflow of a blood centre and a medical institution from a network information system. In each procedure of the blood collecting and supply workflow, the information is read/written by the computer into or from an electronic tag and through the computer information network into the service management information system.

U.S. Pat. No. 8,099,297 describes a business method and system for ordering, purchasing and storing stem cells enabling donors to order and purchase stem-cells from biological tissue sampled from the donor, such as, for example, cord-blood stem cells, wherein the ordering process interfaces directly with attending medical services, and the service steps include collection, extraction, preservation, containment, packaging, delivery and storage of the stem cells.

U.S. Pat. No. 8,229,675 provides a method for managing blood products and tracking their movement in which a database is provided for entering and storing information pertaining to each patient.

U.S. Pat. No. 8,484,049 describes a system for tissue tracking in medical facilities. The tissue tracking system may be incorporated with a supply chain, billing, inventory, and/or order systems and may also track environmental conditions of the tissue during reception, storage and issuance.

EP1238671 provides a bank of cord blood cells from which cells may be withdrawn from storage for both autologous and allogeneic purposes.

EP2263183 relates to a system for the automatic conveyance of biological cells for transplant, therapy or research purposes between withdrawal centres or banks and clinics, transplant centres or research facilities and for the monitoring of the processes from request transmission, for supply of a cell specimen which is suitable for the allogeneic transplant.

U.S. Pat. No. 6,861,954 describes a system for tracking medical products and for associating medical products with a location based on a RFID device signal.

U.S. Pat. No. 8,005,622 describes a system and method for safely transfusing blood to a patient in a computerized healthcare environment. A blood product to be administered to a patient is identified and the patient is identified. A database containing blood compatibility test results is accessed to determine whether the database contains a blood compatibility test result for the identified blood product and identified patient in order to determine whether the test result indicates that the identified blood product is compatible for the identified patient.

U.S. Pat. No. 8,032,306 provides means for identifying a blood product to be administered to a patient by receiving, at a computer at the patient's bedside, a blood product identifier identifying the blood product to be administered to the patient, identifying the patient by receiving at the computer a patient identifier and communicating the blood product identifier and the patient identifier to a blood bank database to maintain a record of the blood product administration.

U.S. Pat. No. 8,204,694 describes systems for automatically tracking blood product administration in a computerized healthcare environment. Information regarding a blood product unit received by the blood bank department is documented in a database. An indication that the blood product unit has been administered to the patient by a healthcare provider is received and the database is automatically updated to reflect that the blood product unit has been administered to the patient.

U.S. Pat. No. 8,666,762 provides a tissue management system for handling tissues such as human cells where the tissue management tracking system prompts and verifies that staff of a medical establishment have handled and used tissue materials in a safe manner.

US20050184153 describes an apparatus for implementing blood sample collection, blood unit requesting, and blood unit transfusion to a patient, comprising a caregiver identity means carrying an electronically readable caregiver code, a patient identification wristband carrying an electronically readable patient code, a reader wherein said reader is capable of reading said caregiver code and said patient code.

US20080189045 provides a method for the collection and distribution of cord blood stem cells using a single collection and distribution entity that applies a uniform protocol to obtain cord blood stem cell samples at each of a plurality of different collection facilities enabling a greater number of samples for both private and public cord blood stem cell banks to be obtained.

US20090299763 describes a method for conducting a stem cell technology business such as a regenerative medicine business using induced pluripotent stem cells (iPSC) and cells differentiated from iPSC where the method provides a database of iPSC-derived cells and methods of using the database for tracking customers and samples.

US20100049542 describes a blood component collection facility comprising a plurality of separately operable blood component collection instruments and a system for networking the blood component collection facility. The networking system provides a system computer linked to a plurality of input devices for tracking donors, operators and blood component collection instruments with respect to one or more blood product collection procedures. The system computer is linked to at least one administrative level computing device to monitor blood component collection activities throughout the blood component collection facility and to facilitate decision making on allocation of donors, operator, and blood component collection instruments.

US20130018356 describes a method for characterizing, preparing, using and disposing of medical equipment such as syringes which are encoded with unique numbers wherein data characterizing a medication container is received from a medication device within a clinical workflow and thereafter, one or more data records are generated, modified or appended to include a portion of the received data.

None of the preceding prior art addresses the problem of optimising processing of biological cellular samples, for example patient samples, in a scalable fashion which provide economies of scale. The present invention addresses this problem and provides improved methods and facilities which can be used to process biological cellular samples such as patient samples in an efficient and scalable manner.

SUMMARY OF THE INVENTION

According to a first aspect of the present invention there is provided a method for parallel processing of a plurality of biological cellular samples comprising i) transferring a plurality of cellular samples (S1 to Sn) to a first processing unit (U1) containing a plurality of identical processing stations (P1/1 to P1/n);

ii) processing each of said cellular samples (S1 to Sn) on a processing station (P1/1 to P1/n) to produce a plurality of processed cellular samples (S1/1 to Sn/1);

iii) transferring said processed cellular samples (S1/1 to Sn/1) to a second processing unit (U2) containing a plurality of identical processing stations (P2/1 to P2/n);

iv) processing each of said cellular samples (S1/1 to Sn/1) on a processing station (P2/1 to P2/n) to produce a plurality of processed cellular samples (S1/2 to Sn/2); and v) transferring to and further processing said plurality of processed cellular samples on one or more processing units (UN) to produce a plurality of processed cellular samples (S1/N to Sn/N).

Having identical processing stations in a unit allows optimisation of the space and services, use of environmental conditions and improves efficiency of processing.

In one aspect, a unit for long duration processes contains more processing stations than a unit for short duration processes. This optimises space usage, reduces capital equipment costs by avoiding the need for additional units, and additionally overcomes any bottlenecks in the processing procedure.

In another aspect, each cellular sample (S1 to Sn) is uniquely identifiable.

In a further aspect, each cellular sample (S1 to Sn) is enclosed in a container, which container is uniquely identifiable. Preferably the container is sterile.

In one aspect, each cellular sample comprises human cells.

In another aspect, the cellular samples are selected from the group consisting of blood samples, tissue aspirates, tissue biopsies, bone marrow, adipose tissue and umbilical cord blood.

In a further aspect, the cellular samples are derived from one or more patients.

In one aspect, the processing of the cellular samples involves one or more processes selected from the group consisting of cell isolation, cell concentration, cell culture, cell expansion, cell transduction and cell formulation.

In another aspect, the method of the invention additionally comprises the step of storing the processed cellular samples (S1/N to Sn/N) in a cell bank.

In a further aspect, the method is an automated method. For example, the method may be carried out using robotic arms under the control of software.

In one aspect, the method additionally comprises the step of administering one or more of the processed cellular samples (S1/N to Sn/N) to one or more patients.

In another aspect, the one or more patients are the original donors of the cellular samples (S1 to Sn). This would be an example of autologous cell therapy.

In a further aspect, the one or more patients are not the original donors of the cellular sample (S1 to Sn). This would be an example of allogeneic cell therapy.

In a preferred aspect, the patient is a cancer patient.

According to a second aspect of the present invention, there is provided a processed cellular sample produced by a method as hereinbefore described.

According to a third aspect of the present invention, there is provided a processed cellular sample as hereinbefore described for use in cell therapy. In one aspect, the processed cellular sample is for use in autologous cell therapy. In another aspect, the processed cellular sample is for use in allogeneic cell therapy.

According to a fourth aspect of the present invention, there is provided a processed cellular sample for use in the treatment of cancer.

According to a fifth aspect of the present invention, there is provided a composition comprising the processed cellular sample as hereinbefore described comprising a biocompatible carrier in a form suitable for mammalian administration.

The "biocompatible carrier" is for example a fluid, especially a liquid or a gel, in which the cellular sample can be suspended, such that the composition is physiologically tolerable, i.e. can be administered to a mammalian body without toxicity or undue discomfort. The biocompatible carrier is suitably an injectable carrier liquid such as a sterile, pyrogen-free aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free, isotonic saline or phosphate buffer.

Alternatively, the "biocompatible carrier" may be in the form of a matrix or scaffold which supports the cellular sample. Natural scaffolds are the total extracellular matrixes of decellularized tissues or organs. In contrast, biomimetic scaffolds may be composed of natural materials, such as collagen or proteoglycans (proteins with long chains of carbohydrate), or built from artificial materials, such as metals, ceramics, or polyester polymers.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

According to a sixth aspect of the present invention, there is provided a cell processing facility for parallel processing of a plurality of biological cellular samples comprising a plurality of processing units (U1 to UN) in which each said unit comprises a plurality of identical processing stations (P1/1 to PN/n) for carrying out a specific process, said processing stations performing a different process in each said unit, wherein the number of processing stations in any one processing unit is varied to optimise the throughput of the cell processing facility.

In one aspect, a unit for long duration processes contains more processing stations than a unit for short duration processes.

In another aspect, the processing station carries out a process selected from the group consisting of cell isolation, cell concentration, cell culture, cell expansion, cell transduction and cell formulation In a further aspect, the cell processing facility additionally comprises a cell bank.

In one aspect, the cell processing facility is located or housed within a hospital or treatment centre.

In another aspect, the cell processing facility is located or housed in a prefabricated building, vehicle, craft, or container for deployment to a location for processing cellular samples and/or cell therapy materials.

In a further aspect, the cell processing facility is located remotely from the site of cell sample collection and/or processed cell sample administration.

In one aspect, the cell processing facility is for use in producing cellular samples for cell therapy such as autologous cell therapy or allogeneic cell therapy. In a preferred aspect, the cell processing facility is for use in producing cellular samples for treating cancer patients.

According to a seventh aspect of the present invention, there is provided a system for parallel processing of a plurality of biological cellular samples comprising processing a plurality of biological cellular samples in a method as hereinbefore described in a cell processing facility as hereinbefore described.

According to an eighth aspect of the present invention, there is provided a computer program product comprising machine instructions operable to configure a data processing apparatus to implement the method as hereinbefore described.

BRIEF DESCRIPTION OF THE DRAWINGS

FIG. 1: Schematic of a unitised parallel processing facility illustrating the workflow of patient samples and processed materials through discrete workflow units comprising processing stations and processing components.

FIG. 2: Schematic of an identity custody chain for patient sample and processed material illustrating means to achieve physical and identity integrity through the use, tracking and recording of uniquely encoded disposable components.

FIG. 4: Schematic of means of providing processing instructions to a processing station from an instruction store.

FIG. 5: Schematic of means of providing processing instructions to a processing station from a processing component.

DETAILED DESCRIPTION OF THE INVENTION

Figure 3:
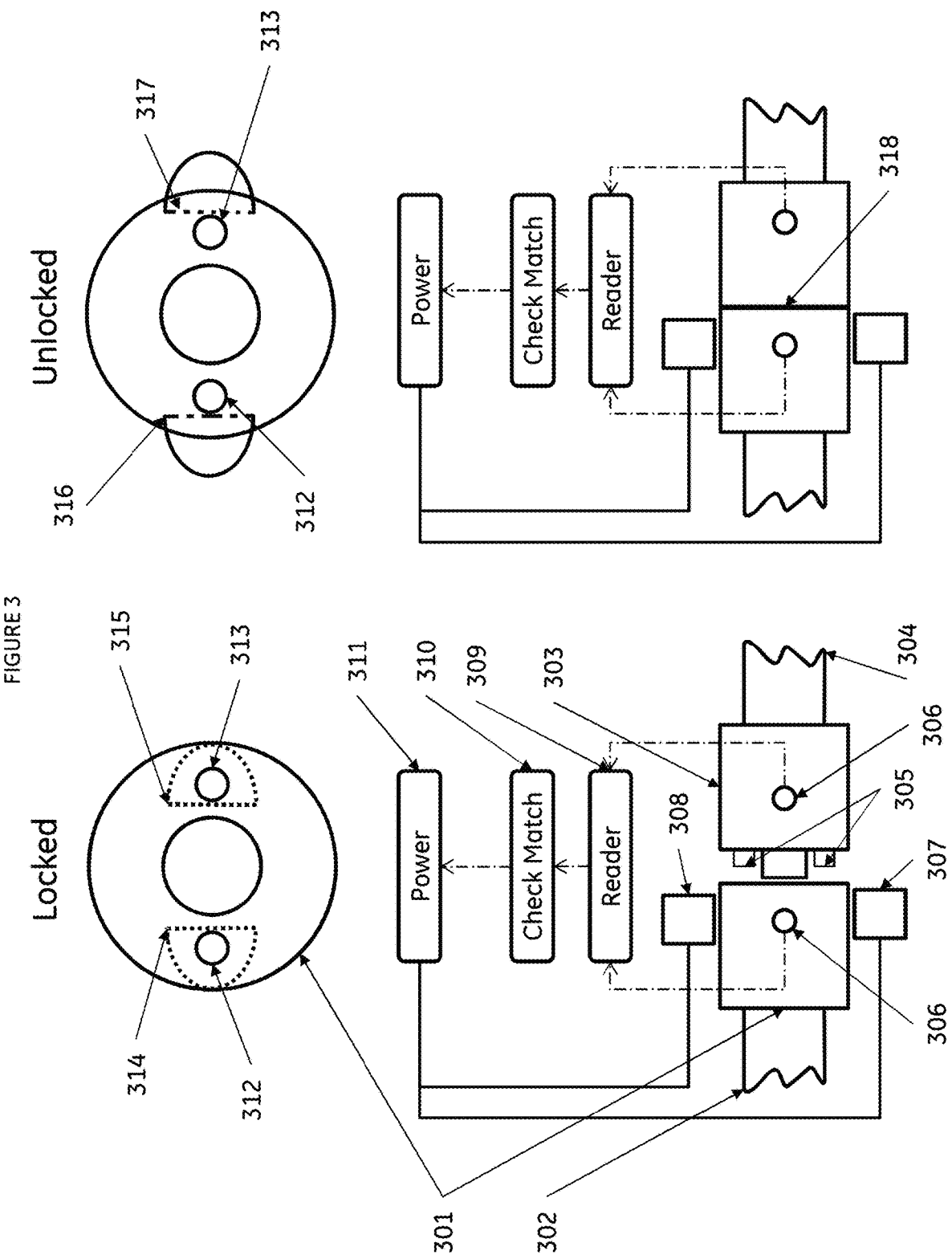
FIG. 3: Schematic of means of maintaining the physical and identity integrity of sample and processed material illustrating means to achieve connection of disposable closed processing components preventing mixing, loss or contamination of sample or processed material through use of encoded connectors.

A scalable cell therapy facility comprises a number of discrete processing units (UNIT 1 to UNIT N) isolated from one another by physical walls, barriers or other demarcation. Each processing unit comprises a number of identical processing stations (P1/1 to P1/n in UNIT 1; P2/1 to P2/n in Unit 2; PN/1 to PN/n in UNIT N) appropriate for the unique processing operation to be carried out within the unit. Patient samples (S1 to Sn) are received by UNIT 1 in uniquely encoded closed sample containers and processed on processing stations P1/1 to P1/n using a separate uniquely coded closed disposable processing component 1 for each sample. Processed samples in closed components appropriate to the workflow stage are sequentially passed through UNIT2 to UNIT N to complete the processing workflow using uniquely coded closed processing components 2 to N at each stage. At each stage of processing transfer of processed patient material from component to component is tracked by recording component unique identities maintaining an identity custody chain.

UNIT 1 to UNIT N may comprise physically separated rooms or zones within a facility with the operations of processing platforms and handling and transfer of components and samples being carried out by one or more operating staff. Alternatively UNIT1 to UNIT N may comprise designated areas within a larger area or room where processing platforms operate automatically and transfer of components and samples is performed by one or more robot devices. The facility comprising UNIT 1 to UNIT N may be housed within a larger facility, such as a hospital or other treatment centre, or may be a self-contained unit capable of independent operation. The facility may be housed in a prefabricated building, vehicle, craft, vessel or other container suitable for deployment to a suitable location for processing cell therapy materials. The facility may be situated locally or remotely to patients providing samples and/or undergoing treatment. Where the facility is located remotely to patient sampling and/or patient treatment locations patient samples and/or final therapeutic materials are transported from and/or to patients in sealed uniquely encoded containers and remote location(s) are connected to the facility by means to allow transmission and receipt of patient and sample identities to provide means to maintain physical and identity integrity for samples and processed materials.

The parallel processing facility maintains physical separation of samples within the processing units by use of disposable closed processing components at all stages in the processing work flow from sample receipt to formulation of the therapeutic material for administration. The facility is readily scalable by increasing the number of processing stations in each unit and the numbers of processing stations in each unit may be tailored to provide the optimum efficiency and throughput to the facility by having a larger number of stations in units where the processing step has a long duration and a smaller number of stations in units which short processing steps (e.g. a small number of stations in the sample isolation unit; a larger number of stations in the cell expansion unit). Segregation of processing stations by function enables the provision of the optimum environment (lighting, electrical power and other services, temperature control etc.) required for the processing stations within a common unit. These characteristics of the unitised parallel processing facility provide a number of key advantages over the shortcomings of conventional duplicated parallel operations where all processes for a single patient are carried out within a separate room (e.g. redundant duplication of equipment, scalability requiring additional space and equipment services).

Figure 1:
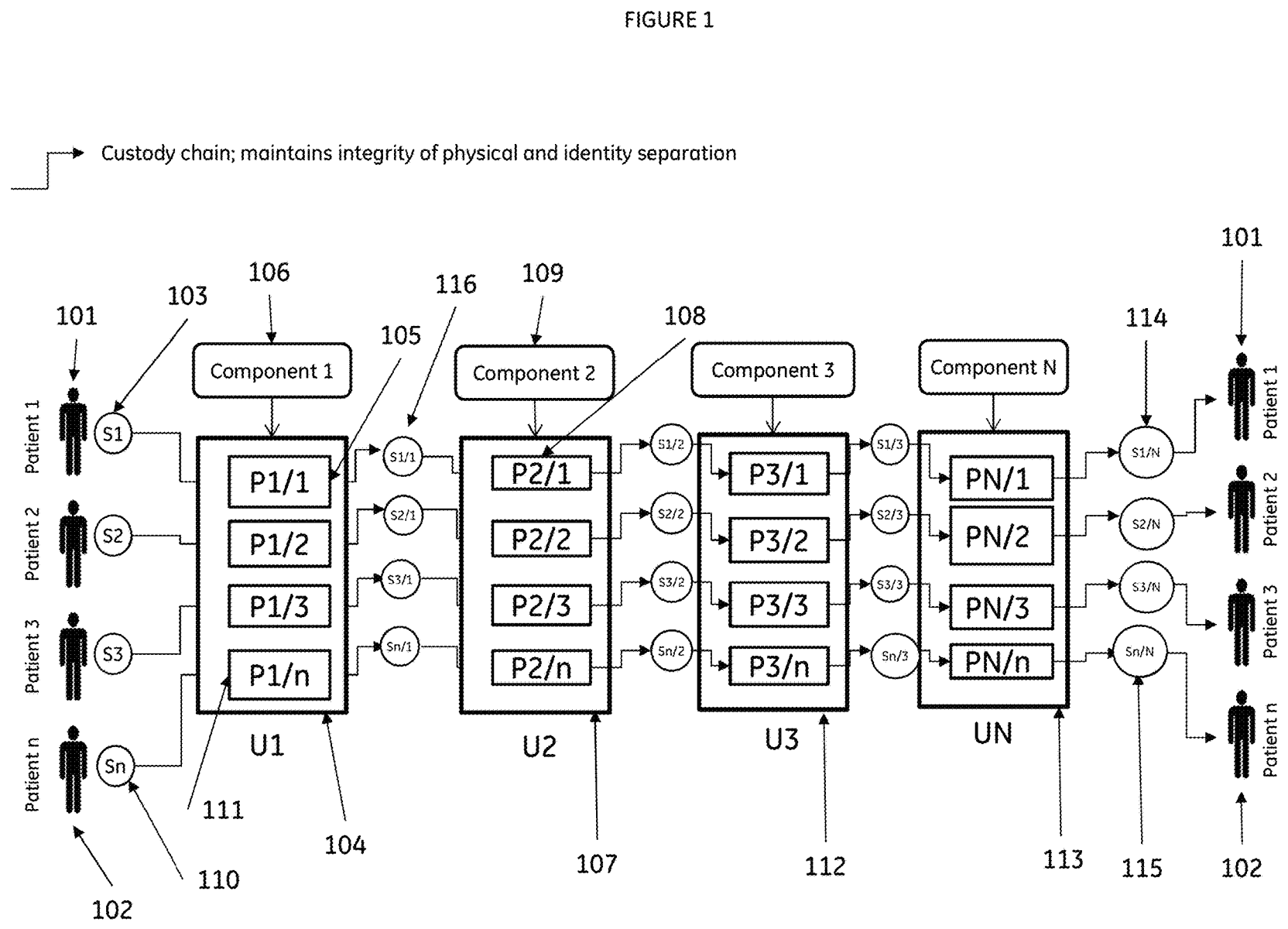

Description of one possible illustrative embodiment of the scalable cell therapy processing facility is made with reference to FIG. 1. The facility comprises a number of processing cells (UNIT 1 to UNIT N) wherein samples from Patient 1 [101] to Patient n [102] are processed in parallel in separate closed disposable containers within the facility to maintain patient sample integrity and identity at all times. A sample S1 [103] containing cells from Patient 1 [101] is collected in a uniquely encoded disposable container and transferred to UNIT 1 [104] to begin processing. UNIT 1 [104] comprises a number of processing stations P1/1 [105] to P1/n [111] suitable for performing the first step in the cell processing work flow. Patient sample S1 [103] is processed on processing station P1/1 [105] using a uniquely encoded disposable processing component 1 [106]. Other samples from Patient 2 to Patient n [102] are processed in parallel with sample n [110] from Patient n [102] processed on processing station P1/n [111] using a uniquely encoded disposable processing component 1 [106]. Following completion of processing in UNIT 1, sample 1 [116] is moved in a closed container to the next processing unit, UNIT 2 [107] for the next stage of processing on processing station P2/1 [108] using a uniquely encoded disposable processing component 2 [109] suitable for the processing operation to be carried out. Processing of samples continues in parallel through processing units UNIT 3 [112] to UNIT N [113] in which the final stage of processing is performed using a separate uniquely encoded disposable processing component for each processing stage and each patient sample. The fully processed therapy sample 1 [114] is transported in a uniquely encoded disposable closed container for administration to Patient 1 [101] from whom the starting sample [103] was taken. Other samples from Patient 2 to Patient n are similarly processed in parallel through the facility at all times being isolated in enclosed uniquely encoded disposable containers with the fully processed therapy sample n [115] being administered to Patient n [102] from whom the starting sample [110] was taken.

The preceding description of one possible embodiment of the present invention is provided for illustrative purposes only. Those skilled in the art will readily appreciate that other means of providing the key required features of the present invention for a unitised parallel processing cell therapy facility are possible.

All components in the processing chain, including an identity bracelet or other identification means worn by the patient, carry unique encoding. Suitable encoding means include but are not limited to encoding using tags in printed, magnetic or electronic form which may be read by light, electronic or magnetic means, such as barcodes, QR codes, RFIDs or transponders. It will be readily understood by those skilled in the art that a variety of encoding means are suitable for use in the method of the current invention. One suitable encoding means comprises light activated micro-transponders, such as those from the PharmaSeq company described in WO2002037721, U.S. Pat. Nos. 5,981,166 and 6,361,950, which are small (500×500×200 μm) low cost silicon devices which store a unique 30 bit read-only identity code and emit the code as radio frequency signal when powered and interrogated with a light emitting reader device. All processing components (sample collection tube, cell purification components, cell culture and expansion components etc.) are pre-registered in a facility component registry where each component's function and intended stage of use in the processing workflow is logged against the component's unique identifier code. In the descriptions of embodiments described herein the term 'transponder' is intended to encompass any means of encoding a unique sample identity which may be read by suitable reading means.

At each stage in the therapy processing workflow the identifier code is read into a unique patient specific record in a central database. The first entry in the database is the identity code from the patient bracelet. At sample collection (e.g. blood collection) the sample collection component identity code is read and two actions are carried out:

1. The sample collection component identity code is checked against the component registry to confirm the correct component is being used for that stage in processing and;
2. The sample collection component identity code is added as the second entry to the custody chain of component identity codes in the patient record.

Following sample collection the filled collection component is transferred to the next operation in the processing workflow to perform a processing step using a processing component specific to that workflow stage and two actions are carried out:

1. The processing component identity code is checked against the component registry to confirm the correct component is being used for that stage in processing and;
2. The processing component identity code is added as the third entry to the custody chain of component identity codes in the patient record.

Processing of the patient sample continues through the necessary operations with each transfer of physical sample from component to component being accompanied by the check and record actions 1 & 2 with the processing components being added as the fourth to the nth entry in the custody chain.

At the end of the processing workflow when the therapeutic material is ready for administration to the patient the following actions are carried out:

1. The identity codes of the component containing the therapeutic material and the patient identity bracelet are both read and;
2. The patient record data base custody chain of component identity codes is checked stepwise to ensure that all component identity codes track back to the same patient identity.

Further features of the custody chain include the ability to link all component identity codes to electronic manufacturer's and/or supplier's batch records whereby scanning of the component appends electronic copies of component batch record files to the patient record file to enable traceability of all components used in processing the patient's sample. In addition all commercially supplied reagents (e.g. cell growth media) carry transponders on their containers with identity codes linked to the manufacture's batch records allowing electronic copies of records, certificates of analysis etc. to be appended to the patient record. To allow for the use of non-commercially supplied, bespoke or other special reagents or formulations which may be prepared within the facility, additional encoded reagent containers are provided for filling and storage of facility produced reagents (e.g. virus preparations for transduction of CAR T-cells in cancer immunotherapy).

These principles are demonstrated in the following illustrative embodiment by reference to FIG. 2. The patient undergoing cell therapy wears an identity bracelet [201] or other non-removable identifying device comprising a unique readable transponder code [202]. The transponder code is read by a reader [203] connected to a central database and the code stored in the patient's individual database record [204]. At the first stage in the cell therapy process a sample, for example of blood, is taken from the patient into a sample collection tube or container [206] carrying a unique transponder code. The transponder code for the sample collection tube or container is read by the reader [203] and the identity code for the filled tube or container stored in the patient's database record [204]. The transponder code is also used to check the component function by reading a component registry [205] containing component functions matched to component transponder numbers for all components in the cell processing workflow. To further process the sample collection tube or container containing the patient's blood sample the sample collection container or tube [206] must be connected to the first component [207] in the processing workflow. Prior to connection the transponder on the first component [207] is read by the reader [203] and checked against the component registry [205] to confirm if the component is the next correct component in the processing sequence. If the component is correct the component transponder code is appended to the patient's database record [204]. If the component is not correct the operator is notified to select the correct component. The sample is sequentially processed through each stage in the workflow using processing components 2 [208], 3 [209], 4 [210] through to processing component n [211] with the number of components determined by the complexity and steps in the workflow. At each stage in sample transfer between components the transponder codes on each component are read by the reader [203], checked against the component registry [205] and recorded in the patient's database record [204]. When sample processing is complete and the therapeutic material is present in the last processing component [211] ready for administration to the patient the transponder code on the component [211] and on the patient identity bracelet [202] are read on the reader [203] and the identity numbers checked against the patient record in the database record [204] to ensure that the transponder identity number for the final component containing the therapeutic material [211] tracks back through the custody chain of successive transponder codes stored in the database record [204] to the same patient identity bracelet [202] transponder code read at sample collection. Matching of all transponder component identity codes in the patient database record [204] confirms that the sample and therapy relate to the same patient in the identity custody chain and therapy can proceed by administration of the sample stored in the final processing container [211].

The described embodiment is provided for illustrative purposes only and those skilled in the art will appreciate that other means of achieving an identity custody chain providing the key features of the invention are possible.

A further key aspect of the present invention is means to achieve a physical and identity custody chain which prevents contamination, cross-contamination or partial or whole loss of a patient sample by environmental exposure in a non-sterile environment or through operator error. All samples and processed materials are handled, processed and stored in closed disposable containers which are specific to each stage of the processing workflow and interface with each processing station in the workflow. All such process components are joined by connection means which prevent:

1. Cross contamination of patient samples by cross-mixing of parallel processing sample workflows being performed in the same processing unit.

2. Loss of patient sample or processed material through the incorrect order of use of components.

To maintain the physical separation and identity of the processed patient sample all connections between processing components 1 to N in the processing workflow are made using connectors furnished with means to prevent loss, mixing or cross-contamination of the sample integrity through operator error. Such connectors are designed and operated to:

A. Allow only the correct sequence of processing components to be used in processing the patient sample preventing loss of the patient sample through use of incorrect components in sequential steps of the processing workflow.

B. Allow only components linked to the patient identity to be coupled together preventing mixing or cross-contamination of the sample with another sample being processed through the facility in parallel.

C. Maintain a record of the identity of the patient sample at all stages in the workflow preventing mixing or cross-contamination of the sample with another sample being processed through the facility in parallel.

D. Prevent the re-use of components preventing mixing or cross-contamination of the sample with another sample being processed through the facility in parallel.

These principles are demonstrated in the following illustrative embodiment by reference to FIG. 3. Connectors providing sample physical and identity integrity comprise a female [301] connector linked via tubing [302] to a first processing component and a male connector [303] linked via tubing [304] to a second processing component. The male connector [303] and the female connector [301] are designed so as to form a liquid- and air-tight junction between two components when correctly connected. The connectors are further provided with means to establish a sterile connection when connectors are joined together in a non-sterile environment, such as that described in U.S. Pat. No. 6,679,529. The male connector [303] carries blocking pins [305] orientated to fit into location holes [312 & 313] located in the front face of the female connector [301]. The blocking pins are prevented from entering the location holes [312 & 313] by metal blocking shields [314 & 315] held in slots within the female connector [301] which prevent coupling of the connectors to form a junction between the processing components. The male and female connectors carry identity transponders [306] encoding the individual identities of the processing components attached to each of the connectors. To form a join between the connectors the male [303] and female [301] connectors are placed in a reading device [309] comprising means to align the connectors and means to read information from the identity transponders [306] carried on each connector. On activation of the reader [309] the identity codes of the two connectors are read and the device software performs a component compatibility match check [310] to determine whether the two connectors present in the device form a correct sequential component coupling for sample processing. Additional checking is performed by the reader [309] software to further ensure the physical separation and identity of the patient sample, for example the identity codes from the transponders [306] are checked to ensure that the component being offered to receive the patient sample at a step in the processing workflow is not a waste component having been previously used. If the match checking operation [310] confirms the correct identity of the paired connectors a power supply [311] is activated to energise electromagnets [307 & 308] held within the reading device. Activation of the electro magnets pulls the blocking shields [314 & 315] outwards and away from the location holes [312 & 313] in the female connector to an open position [316 & 317] allowing the blocking pins [305] in the male connector to enter the location holes [312 & 313] in the female connector. The connectors are now pushed together to provide a secure operating connection [318] between the processing components. Following correct connection the reader [309] additionally records the identity code of each connector from the transponders [306] and sends the data to the patient sample record to provide a sample identity custody chain. If the match checking operation [310] detects that the two connectors do not have the correct identities to form a correct sequential component coupling for sample processing, power is not supplied to the electromagnets [307 & 308] preventing the coupling of the connectors. The reader software then prompts the operator to select the correct components to form an operable connection.

The described embodiment is provided for illustrative purposes only and those skilled in the art will appreciate that other means of providing component connection meeting the required principles of maintaining sample physical and identity integrity may be used. Such means include but are not limited to alternative methods of component encoding such as barcoding, and magnetic strip and RFID tagging to identify correct components for connection. Alternative means for prevention of connection of incorrect sequential components include but are not limited to providing a sequential series of unique connectors with varying mirrored dispositions of pins and holes or grooves and ridges which physically preclude the connection of mismatched connectors. Such connection means can be designed and disposed to ensure that the output from a first component will connect only to the input of a second component, the output from the second component will connect only to the input of a third component and so on for a series of N components with the output of the N-Ith component connecting only to the input of the Nth component in the series. Additionally the connectors may be colour and or shape coded to aid in manual or automated selection of correct components and connection pairings.

A further key aspect of the invention is the provision of processing instructions to a processing station directly from, or in response to, a processing component connected to a processing station. Each processing component comprises means to instruct a processing station on the type of processing component and if applicable, the variant type of the processing component and to instruct a processing station on processing the patient sample held within the processing component. A processing component variant type may comprise a different size, capacity or other feature of the component which requires individual processing instructions specific to that variant. Such individual processing instructions may have variant specific instructions for reagent volumes, pressures, flow rates, incubation times etc. which are specific for the optimum operation of that processing component variant. For example a processing component for performing cell isolation may be provided in two variants for processing different volumes of blood; such variants will require different reagent volumes and hence different processing instructions. Similarly a processing component used for cell expansion, such as a disposable bioreactor for cell culture, may be provided in different sizes and culture capacities to allow the growth of different numbers of cells for use in therapy; such variants will utilise different volumes of culture media and different processing instructions.

Linking processing instructions to a processing component and providing such instructions to a processing platform operably connected to the processing component provides:

a) means to ensure that the instructions for processing a patient sample within the processing component are correct for that component, obviating risk of sample loss through use of incorrect processing instructions.

b) means to ensure that variants of processing components performing the same operation at a different scale are provided with specific processing instructions necessary for the correct processing.

c) means to remove operator errors by directly instructing processing stations.

d) means to permit processing to be carried out in an automated environment using robotic means to achieve the processing workflow where each processing station in the workflow is appropriately instructed to perform a processing operation on receipt of a processing component.

Figures 4, 5:
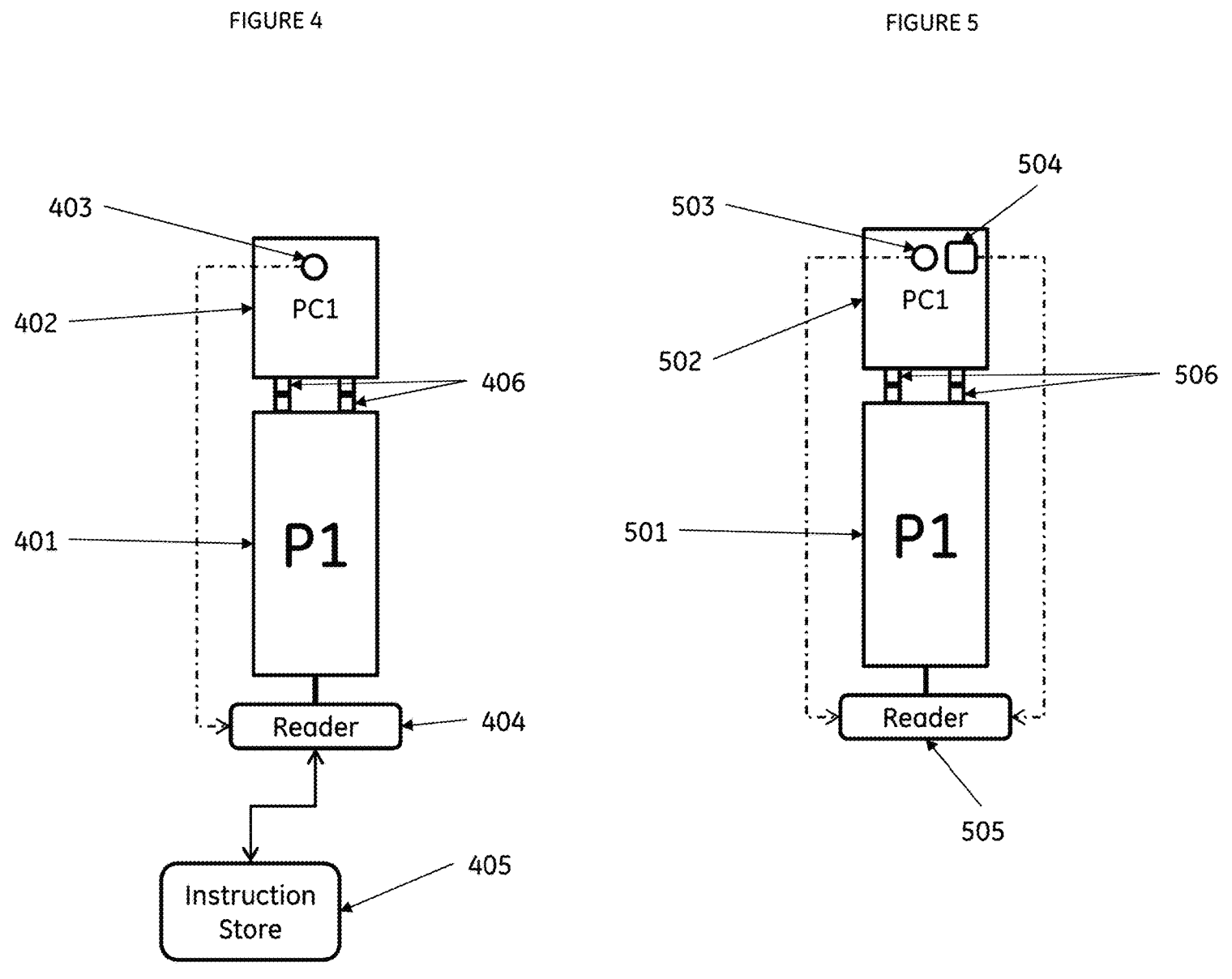

These principles are demonstrated in the following illustrative embodiments by reference to FIG. 4. In a first further embodiment of the invention a processing component [402] is operably connected to a processing station [401] by connectors [406] to permit sample processing wherein the processing component comprises a transponder [403] carrying a unique identity code. The unique identity code is linked to a database in a central instruction store [405] to specific processing instructions for the type and variant of processing component carrying the transponder [403]. The identity code carried by the transponder [403] is read by a reader [404] connected to the processing station [401] and checked to confirm that the processing component is of the correct type for processing on the processing station [401]. On receipt of the identity code the reader [404] retrieves processing instructions from the instruction store [405] by wired or wireless communication and the received instructions are passed to the processing station [401] to permit the correct operation of the processing station in processing the patient sample contained in the processing component [402].

In a second further embodiment of the invention (FIG. 5) a processing component [502] is operably connected to a processing station [501] by connectors [505] to permit sample processing wherein the processing component comprises a transponder [503] carrying a unique identity code. The processing component [502] additionally comprises a stored processing instruction set [504] specific to the type and variant of the processing component [502]. The identity code carried by the transponder [503] is read by a reader [505] connected to the processing station [501] and checked to confirm that the processing component is of the correct type for processing on the processing station [501]. The processing instruction set [504] is also read by the reader [505] by wired or wireless means and the processing instructions passed to the processing station [501]. The processing instruction set [504] carried by the component [502] may be stored and read by a variety of means including, but not limited to, storage of processing instructions by barcoding, QR coding, magnetic and solid state memory, and reading of processing instructions by optical or electronic means. In a further variant identity coding and instruction storage may comprise a single data store carried on each processing component.

In a further embodiment analytical means are used to ensure matching of a patient sample and a therapeutic material derived from the sample to ensure identity integrity is maintained through processing. The patient sample is subjected to a suitable chemical, biochemical or molecular analysis and a first biomarker signature characteristic of the sample is stored on the patient's database record. Following processing of the sample the resulting therapeutic material is analysed using the same analytical method and a second biomarker signature is stored on the patient's database record. Prior to administration of the therapeutic material the first biomarker signature of the original patient sample and the second signature of the therapeutic material are checked to verify a match between the two signatures confirming that the patient sample and the processed material are both derived from the same patient.

Suitable analytical means include, but are not limited to, analysis of proteins, RNA and DNA. Suitable means for deriving a signature of protein biomarkers include analysis of cellular proteins, including but not limited to, HLA antigens and blood group proteins by flow cytometry, ELISA or western blotting. Suitable means for deriving a signature for RNA and/or DNA include, but are not limited to, PCR, RT-PCR, DNA sequencing, SNP analysis, RFLP analysis, genetic fingerprinting and DNA profiling. Particularly suitable methods include those in standard use in forensic medicine which analyse DNA repeat sequences that are highly variable such as variable number tandem repeats (VNTR) and in particular short tandem repeats (STR) which are so variable that unrelated individuals are extremely unlikely to have the same VNTR. Such means can be used to unambiguously assign a patient identity to a processed therapeutic material by matching the STR signature of the original patient sample and the therapeutic material.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A method for parallel processing of a plurality of biological cellular samples comprising:

i) transferring a plurality of cellular samples (S1 to Sn) to a first processing unit (U1) comprising a plurality of processing stations (P1/1 to P1/n);

ii) processing in parallel said plurality of the cellular samples (S1 to Sn) on the processing stations (P1/1 to P1/n) to produce a first plurality of processed cellular samples (S1/1 to Sn/1);

iii) transferring said first plurality of processed cellular samples (S1/1 to Sn/1) to a second processing unit (U2) containing a plurality of processing stations (P2/1 to P2/n); and v) processing in parallel each of said first plurality of processed cellular samples (S1/1 to Sn/1) on a processing station (P2/1 to P2/n) to produce a second plurality of processed cellular samples (S1/2 to Sn/2);

wherein in step ii) the processing of the plurality cellular samples (S1 to Sn) on the processing stations (P1/1 to P1/n) of the first processing unit (U1) comprises varying at least one processing instruction between at least two of the processing stations (P1/1 to P1/n), wherein each of said plurality of processing stations (P1/1 to P1/n) performs a process which is the same type of process, wherein the process is selected from the group consisting of cell isolation, cell concentration, cell culture, cell expansion, cell transduction, and cell formulation.

2. The method according to claim 1, wherein varying the at least one processing instruction comprises varying at least one of reagent volume, pressure, flow rate, and incubation time.

3. The method according to claim 1, wherein processing of the plurality cellular samples (S1 to Sn) on the processing stations (P1/1 to P1/n) comprises cell culturing or cell expanding.

4. The method according to claim 1, wherein each of the cellular samples (S1 to Sn) is enclosed in container.

5. The method according to claim 1, wherein said method is an automated method.

6. The method according to claim 5, wherein at least one robotic arm is used to automate the method.

7. The method according to claim 1, wherein said first plurality of processed cellular samples (S1/1 to Sn/1) are transferred to the second processing unit (U2) containing a plurality of processing stations (P2/1 to P2/n) via tubing.

* * * * *